(12) United States Patent
Cline

(10) Patent No.: US 6,210,384 B1
(45) Date of Patent: Apr. 3, 2001

(54) CONVEX INSERT SYSTEM FOR AN OSTOMY APPLIANCE

(75) Inventor: John B. Cline, New Brunswick, NJ (US)

(73) Assignee: Bristol-Myers Squibb Company, New York, NY (US)

( * ) Notice: Subject to any disclaimer, the term of this patent is extended or adjusted under 35 U.S.C. 154(b) by 0 days.

(21) Appl. No.: 09/211,302

(22) Filed: Dec. 15, 1998

Related U.S. Application Data

(60) Provisional application No. 60/068,332, filed on Dec. 18, 1997.

(51) Int. Cl.[7] ........................................................ A61F 5/44
(52) U.S. Cl. ................................ 604/338; 604/342
(58) Field of Search ...................... 604/338, 339, 604/332, 342

(56) References Cited

U.S. PATENT DOCUMENTS

| 5,163,930 | * | 11/1992 | Blum ................................ 604/338 |
| 5,693,036 | * | 12/1997 | Kilgour ............................. 604/338 |
| 5,730,735 | * | 3/1998 | Holmberg et al. ............. 604/342 X |
| 5,947,941 | * | 9/1999 | Leise, Jr. et al. ............... 604/339 X |

FOREIGN PATENT DOCUMENTS

WO93/18725 * 9/1993 (WO) .................................. 604/338

* cited by examiner

*Primary Examiner*—John B. Yasko
(74) *Attorney, Agent, or Firm*—Stuart E. Krieger

(57) ABSTRACT

A convex insert system for an ostomy appliance includes a convex insert and a mounting member on the inner wall of an annular coupling. When the convex insert is mounted on the mounting member, the appliance has a convex curvature which when properly positioned helps the patient's stomal to protrude.

9 Claims, 5 Drawing Sheets

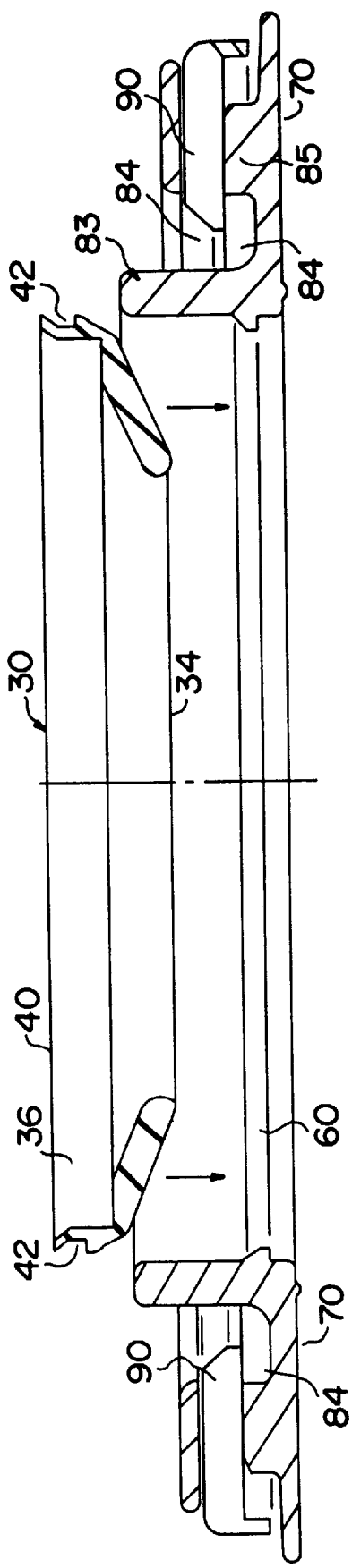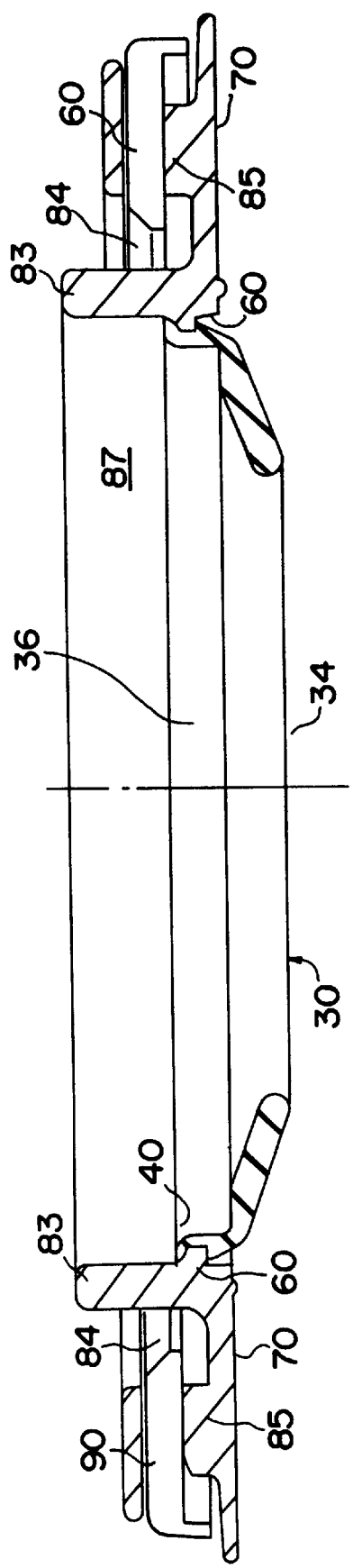

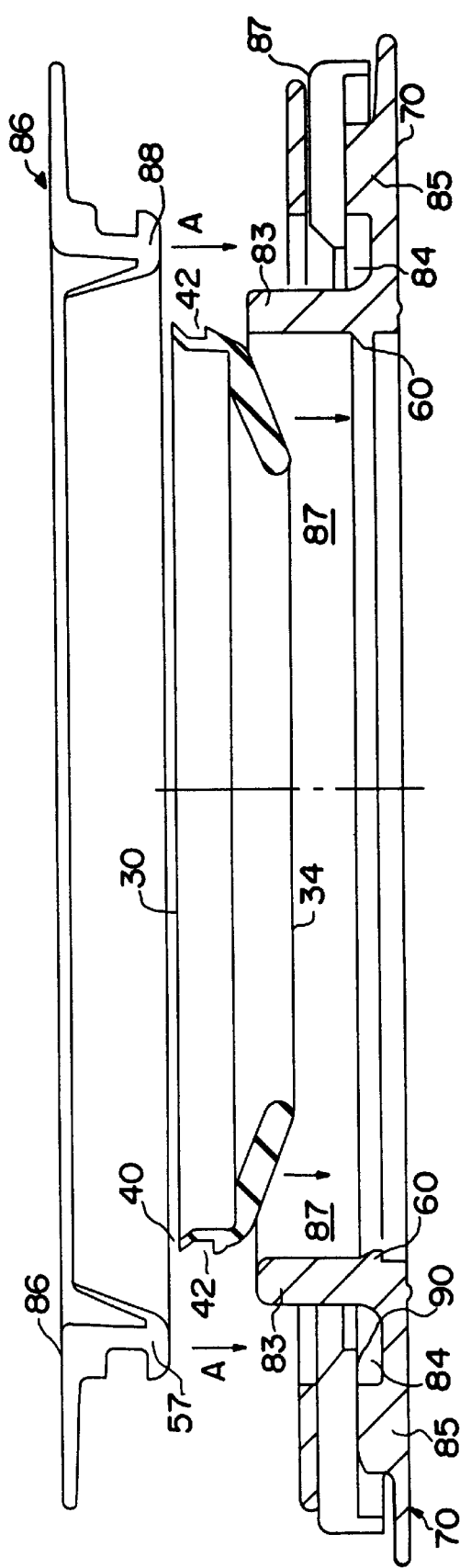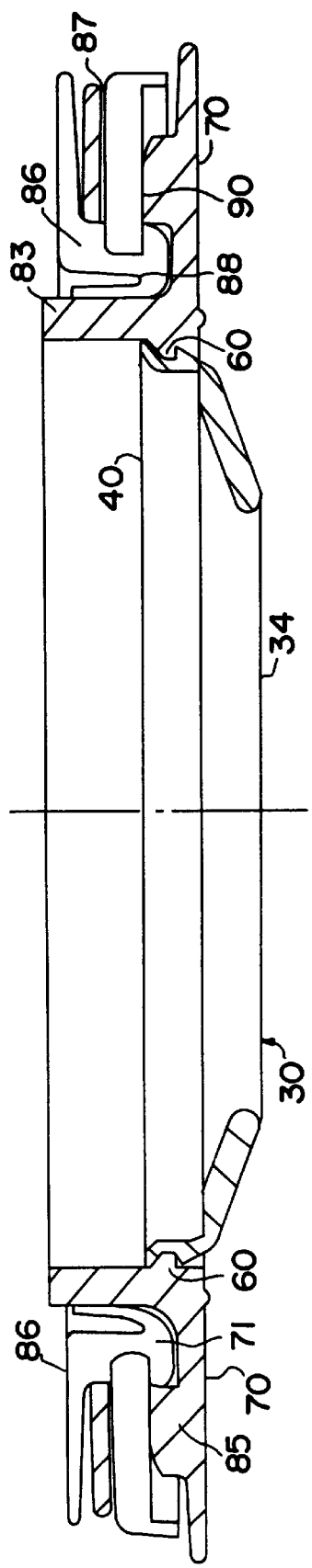

CONVEX INSERT SYSTEM FOR AN OSTOMY APPLIANCE

This application claims benefit of provisional application Ser. No. 60/068,332 filed Dec. 18, 1997.

BACKGROUND OF THE INVENTION

The present invention relates to ostomy appliances and more particularly to an insert attachable to an ostomy coupling so as to provide it with a convex curvature.

Various kinds of ostomy devices are known in the art. A two piece ostomy device typically includes a faceplate having two sides with an adhesive dressing on one side that adheres to the peristomal area of the patient's skin and a pouch which is removably affixed to the opposite side of the faceplate. When a coupling system is employed with a two piece ostomy device, a first coupling member in the form of a plastic ring surrounds an opening in the faceplate which receives the stoma. A second coupling member, also in the form of a plastic ring, is bonded to the ostomy bag around the inlet opening. The first coupling is secured to the second coupling. This can be accomplished by providing the first coupling ring with a rib and the second coupling ring with a channel as described in U.S. Pat. No. 4,460,366 issued Jul. 17, 1984 to Steer, et al. The rib of the first coupling is dimensioned so as to lodge within the channel of the second coupling ring.

A convex insert is particularly helpful in situations where the stoma does not sufficiently protrude beyond the abdominal skin surface or where the muscle surrounding the stoma lack rigidity. In these situations the flat surface of the faceplate does not provide a fluid tight and weight supporting seal. Also, it is considered desirable to cause a stoma that does not normally protrude to protrude into the ostomy appliance. In order to address these situations a faceplate with a convex curvature which is created by a convex insert is considered desirable. The convex insert is secured around the stoma so as to apply pressure against the patient's abdomen thereby causing the stoma to protrude.

U.S. Pat. No. 5,163,930 to ConvaTec discloses a convex insert that is designed for use with a coupling ring having an axially extending rib. The insert is securely lodged under the radially extending surface which partially defines the rigid sealing flange. The insert includes a convex annular body with an arcuate relatively non-deformable portion and a deformable circumferential portion. The deformable portion has an outer edge with a circumference normally slightly larger than the inner circumference of the sealing flange. The circumference of the deformable portion is temporarily reduced as the convex insert is inserted into the coupling ring. Once the insert is positioned under the flange surface, the circumference of the insert returns to its normal surface and the insert is securely seated. The convex insert disclosed in this patent cooperates with and is in contact with the axially extending rib of the coupling ring.

It is an objective of the present invention to provide a convex insert system separate from the portions of the body side and pouch side couplings that join the couplings together.

It is a further objective of the present invention for the convex insert to form a circumferential seal with the coupling on which it is mounted.

SUMMARY OF THE INVENTION

The convex insert of the present invention is entirely resiliently deformable. The resiliently deformable body of the insert includes a circumferential edge and at least one projection or tab, but preferably a plurality of projections or tabs, on its outer surface. The projections are is positioned proximate to the circumferential edge. The convex insert is mounted on an ostomy coupling. The coupling is preferably a circular body-side coupling have a central opening. The coupling includes an annular surface around the opening. The opening fits around the patient's stoma. The inner surface of the coupling includes a radially projecting rib extending at least partly circumferentially around the inner surface. The rib preferably extends around the entire circumference. When deformed the convex insert is capable of insertion into the annular inner surface so that the projection is lodged against the radially extending rib so that the convex insert is captured within the opening upon its resilient return into a substantially undeformed condition.

The convex insert system works well with a modified version of the three piece locking system disclosed in U.S. Pat. Nos. 5,662,628 and 5,662,629, commonly assigned herewith. The three piece system includes a body side coupling, pouch side coupling and a locking ring. Pursuant to the present invention a coupling is modified so as to include a radially projecting rib on its inner annular surface.

It is possible to mount the convex insert on a bag-side coupling that is properly modified to include an inwardly projecting rib.

BRIEF DESCRIPTION OF THE DRAWINGS

The invention will be better understood from the following description of an illustrative example thereof, given with reference to the accompanying drawings in which:

FIG. 1 is a cross-sectional view of a convex insert system pursuant to the present invention wherein the convex insert is in position for insertion within the opening of a coupling;

FIG. 2 is a cross-sectional view of the convex insert system of claim 1 wherein the convex insert has been inserted;

FIG. 3 is a cross-sectional view of a three piece ostomy device including a bag-side coupling, body-side coupling and locking ring, wherein the bag-side coupling is in position for coupling to the body-side coupling and the convex insert is in position for insertion;

FIG. 4 is a cross sectional view of the three piece ostomy device of FIG. 3 wherein the bag-side coupling is coupled to the body-side coupling and the convex insert is inserted;

DETAILED DESCRIPTION OF THE DRAWINGS

Referring to FIGS. 1–8, the present invention is a convex insert system which includes a convex insert 30 and a mounting member in the form of a projecting rib 60 onto which the convex insert 30 is mounted.

Figure 5:
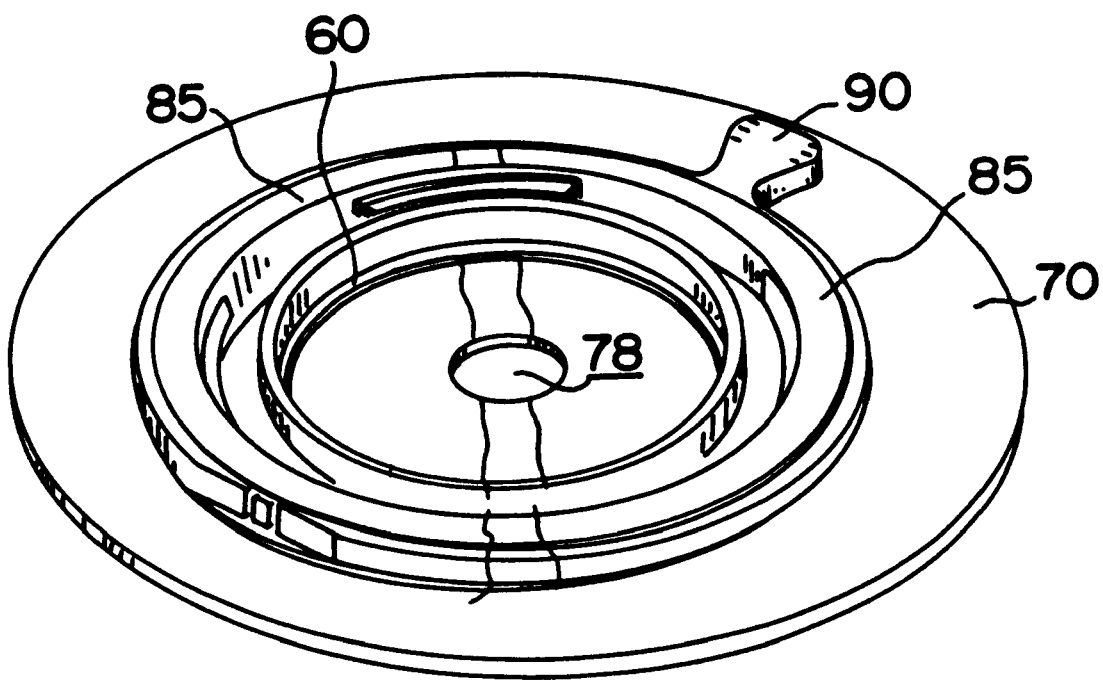
FIG. 5 is a perspective view of the top of a coupling of a convex insert system in accordance with the present invention.
Figure 6A:
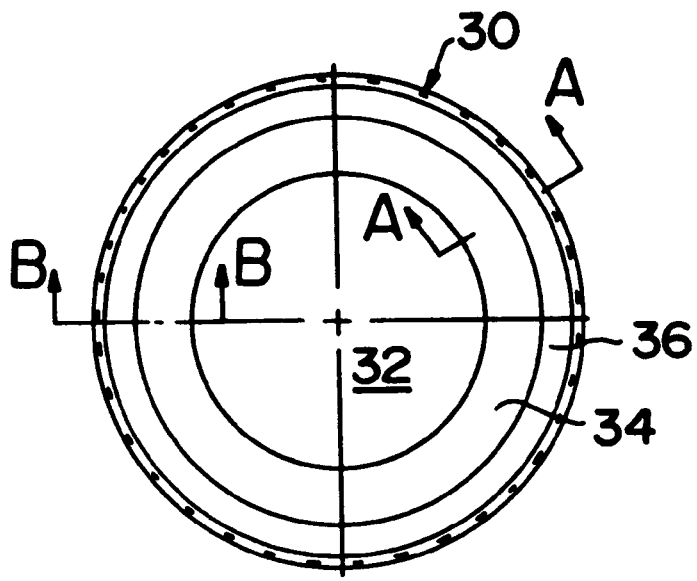
FIG. 6A is an elevational view of the bottom of a convex insert of a convex insert system pursuant to the present invention.
Figure 6B:
FIG. 6B is a plan view of the side of a convex insert of FIG. 6A.
Figure 6C:
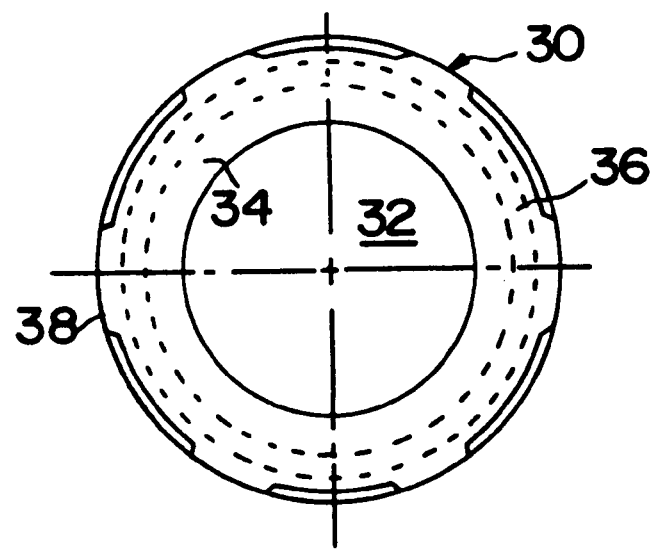
FIG. 6C is an elevational view of the top of a convex insert of FIG. 6A.
Figure 7:
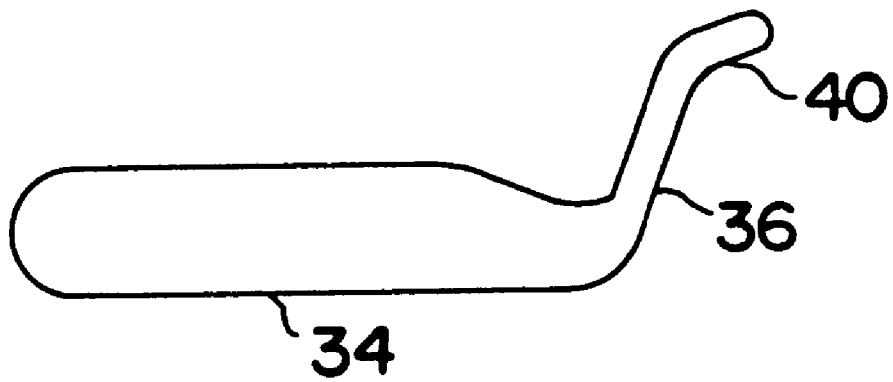
FIG. 7 is a view along lines A—A of FIG. 6.
Figure 8:
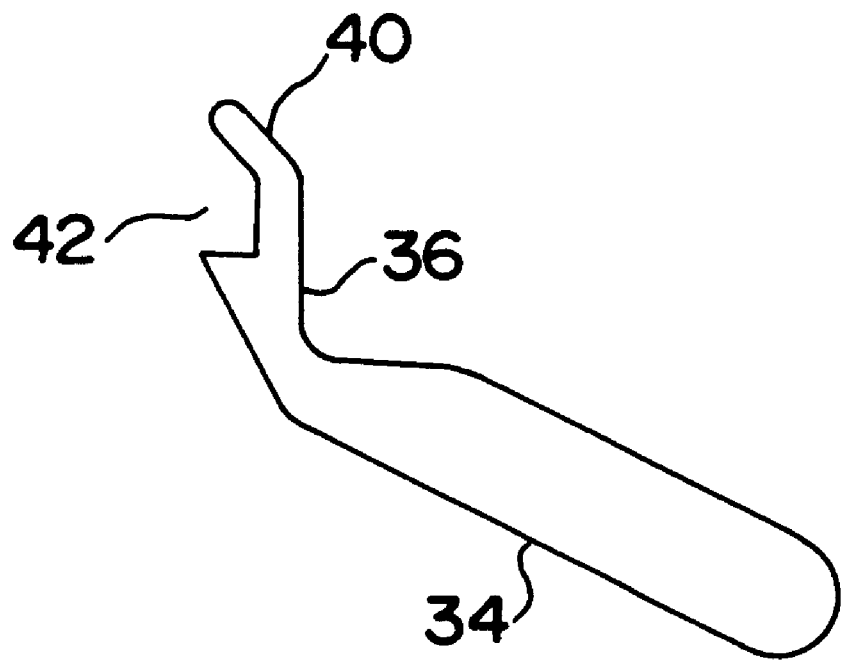
FIG. 8 is a view a long lines B—B of FIG. 6.

The convex insert 30 has a deformable body preferably made of plastic. A central opening 32 in the convex insert 30 fits around the stoma (not shown). The convex insert 30 includes an inner convex shaped portion 34, and a circumferential skirt portion 36 extending therearound. The skirt portion 36 has a plurality of projecting tabs 38 spaced circumferentially about the skirt portion 36 and a circumferential protruding rim portion 40. A slot portion 42 for accommodating a mounting member 60 therein is present between the tabs 38 and rim portion 40. The slot portion 42 is not present in the skirt portion 36 where the tabs 38 are absent (FIGS. 6 and 7).

The convex insert 30 is mounted onto a bodyside flange 70 having a circumferential rib 72. The body-side flange is mounted on a surface of a faceplate having two planar surfaces. On the opposite surface is adhesive for attaching the faceplate to the patient's body. As shown in FIGS. 1–5, a body-side flange 70 includes an inner wall 76 surrounding a central opening 78. A mounting member or projecting rib 60 extends radially inward towards the center of the central opening 78 from the inner wall 76. The mounting member or projecting rib 60 is preferably on a body-side flange 70, however, it is possible to put a mounting member on the bag-side flange. The body-side flange 70 is mounted on a faceplate which includes an adhesive surface for attaching the flange 70 to a patient's abdomen about the stoma (not shown). The body-side flange 70 includes a channel 84 for receiving a bag-side flange 86. The channel 84 is between the inner wall 83 and an outer wall 85. The outer wall 85 includes an aperture 89 permitting the projection of a portion of a locking ring 90 through the outer wall 85 and into the channel 84.

FIG. 3 shows the position of the bag-side flange 86 prior to the coupling of the bag-side flange 86 and body-side flange 70 together. The rib 90 is shown on the inner surface 87 of the inner wall 83 and the convex insert 30 is in position for insertion.

FIG. 4 shows the position of the bag-side flange 86 within the channel 84 of the body-side flange 70 with a locking ring 90 locking both flanges 70, 86 together. The convex insert 30 is shown mounted on the mounting member 60.

In order to mount the convex insert 30 on the inner wall 83 it is manually manipulated into the position shown in FIGS. 1 and 3 and pushed in the direction of the arrows A into the position shown in FIGS. 3 and 4. Similarly, the bag-side flange 86 is coupled to the body-side flange 70 by manual manipulation into the position shown in FIG. 3 and pushed in the direction shown in FIG. 4 until the flanges 70, 86 couple. FIGS. 1 and 2 include the body-side flange 70, locking ring 90 and convex insert 30. The bag-side flange 86 is omitted.

The bag-side flange 86 includes a sealing strip 88 (FIGS. 3 and 4) which aids in sealing the channel 84 and deterring the leakage of stomal effluent through the coupled flanges 70, 86.

The convex insert 30 is mounted onto the mounting member 60 independently of the coupling of flanges 70, 86. Since the insert 30 is separate from the channel 84 and sealing strip 88 because the mounting member 60 is on the inner surface 87 of the inner wall 83 no interference occurs between the coupling of coupling members 70, 86, and the insertion of the convex insert 30.

The convex insert 30 is moved within the inner wall 83 into position to be mounted on the mounting member 60 and subsequently pushed into place onto the mounting member 60. The convex insert 30 resiliently deforms so that the mounting member 60 fits into the insert slot portion 42 and when in place it resiliently returns to its undeformed or normal condition. The convex insert 30 preferably seals against the inner surface 87 so that any stomal effluent is conducted through the convex insert 30 and into the pouch.

As various changes can be made to the above convex insert system without departing from the scope of the invention, it is intended that all matter contained in the above description or shown in the accompanying drawings shall be interpreted as illustrative. It is intended herein to cover all the variations and modifications which fall within the scope of the present invention, as defined by the following claims.

What is claimed is:

1. A convex insert system for an ostomy coupling comprising:
    a first circular ostomy coupling having an opening, said coupling including an inner annular surface around said opening for fitting around a user's stoma, said inner annular surface having an inwardly radially projecting rib extending at least partly circumferentially therearound, said inner annular surface including an axially extending portion having a distal top surface; and
    a convex insert having a resiliently deformable body with a circumferential edge and outer convex surface, said body including a slot portion proximate to said circumferential edge, said convex insert being instable when deformed within said inner annular surface so said rib is captured said slot portion and said convex insert is secured within said inner annular surface entirely below said distal top surface, said convex surface axially projecting from said coupling for directly contacting the user's body.

2. The convex insert system of claim 1 wherein said convex insert firer includes at least one tab projecting from said body, said slot portion being between said tab and said circumferential edge.

3. The convex insert system of claim 1 wherein at least one tab includes a plurality of tabs spaced circumferentially and proximate to said circumferential edge.

4. The convex insert system of claim 1 wherein said convex insert has a central opening for fitting around said stoma.

5. The convex insert system of claim 1 wherein said convex insert is substantially undeformed when rib is captured in said slot portion.

6. The convex insert system of claim 1 further comprising a second coupling securable to said first coupling without contacting said convex insert.

7. The convex insert system at claim 1 wherein said first coupling is secured to one surface faceplate, one surface of said faceplate having an adhesive for securement to a patient's skin.

8. The convex insert system of claim 1 further comprising a planar faceplate having two opposite surfaces, said first coupling being mounted on one of said opposite surfaces, a medical adhesive being mounted on said other of said opposite surfaces for attachment to a patient's body, said first coupling having an annular channel adapted to capture an annular sealing strip therein, said second coupling having an annular sealing strip adapted to be captured in said channel.

9. The convex insert system of claim 8 wherein said convex insert system further includes a releasable locking ring mounted on said first coupling, said locking ring locking said first coupling to said second coupling in a first position, and releasing said first coupling from said second coupling in a second position.

* * * * *